United States Patent [19]

Schoendorfer et al.

[11] Patent Number: 4,675,106
[45] Date of Patent: Jun. 23, 1987

[54] PIVOT PIN BEARING FOR BIOMEDICAL SYSTEMS

[75] Inventors: Donald W. Schoendorfer, Santa Ana; Warren P. Williamson, IV, Huntington Beach, both of Calif.

[73] Assignee: Hemascience Laboratories, Inc., Santa Ana, Calif.

[21] Appl. No.: 722,707

[22] Filed: Apr. 12, 1985

[51] Int. Cl.⁴ .................. B01D 35/00; B01D 45/14
[52] U.S. Cl. ........................... 210/232; 210/380.1; 210/541; 210/542
[58] Field of Search .............. 210/433.2, 927, 360.2, 210/321.1, 304, 780, 781, 782, 232, 361, 380.1, 541, 542

[56] References Cited

U.S. PATENT DOCUMENTS 3,448,858  6/1969  Delcellier et al. ............ 210/433.2

Primary Examiner—Frank Sever
Attorney, Agent, or Firm—Bogucki, Scherlacher, Mok & Roth

[57] ABSTRACT

In a disposable biomedical system for processing fluids in a closed environment such as a plasmapheresis system, comprising a plastic rotor mounted for rotation on a pivot pin bearing and a seal, particularly a silicone lubricated O-ring seal, between the rotor and pin, the improvement wherein said pivot pin is a molded pivot pin of a hard plastic material having a low coefficient of friction and lubriciousness, and which is capable of being irradiated by gamma radiation for sterilization and modification of the plastic material without degradation or loss of lubricious properties. The pivot pin bearing preferably comprises an injection molded polyamide based resin.

22 Claims, 5 Drawing Figures

PIVOT PIN BEARING FOR BIOMEDICAL SYSTEMS

BACKGROUND OF THE INVENTION

This invention relates to biomedical systems for fluids separation embodying a rotor mounted on a pivot pin bearing, and is particularly concerned with medical disposable units involving rotation of a molded plastic part suspended on pivot pin bearings, especially for applications involving the rotation of a filtration support housing or for the rotation of a centrifugal separation housing. A particular area of usefulness of the present invention is in hemapheresis, relating to the separation of one or more constituents of blood, using disposable filtration or centrifugal separation devices. A specific area of application is in a plasmapheresis disposable separation device for the filtration of plasma from whole blood.

Plasmapheresis devices presently employed include membrane filtration devices as exemplified by the device disclosed and claimed in application Ser. No. 449,470, filed Dec. 13, 1982 for "Blood Fractionation System And Method" by H. Fischel. Such membrane filtration device has an interior spinner which is covered with a filter membrane and includes a conduit system for collecting the plasma passing through the membrane. The device receives an input fluid such as whole blood which passes into the space between the spinner and the outer wall of the housing. The plasma in the blood is filtered through the membrane into corrugations on the surface of the spinner, from which the plasma passes through holes into a central conduit and passes out at the bottom through an outlet conduit concentric with the central axis of the device.

The spinner is mounted in a closed cell or housing, and is driven remotely. This is accomplished by providing a magnetic coupling device at the top of the spinner. An external magnetic drive has one or more magnets which attract and lock onto the internal magnetic coupling device of the spinner. As the outer drive magnet is spun the inner magnetic coupling device is driven synchronously with the drive magnet to rotate the spinner, for example, at 3600 rpm. The magnetic coupling device may be either a piece of magnetic permeable material or another magnet oriented to attract the drive magnet as described in "Rotor Drive For Medical Disposables" by W. Williamson et al, Ser. No. 727,585, filed Apr. 26, 1985.

A pivot pin bearing is mounted at the top of the device to hold the upper end of the spinner during rotation, and a second pivot pin bearing is mounted at the bottom of the device on which the spinner rests during rotation. As the spinner is rotated by the external magnetic drive, blood passing into a gap or space between the rotating filter membrane of the spinner and an inner wall of the housing passes around the surface of the periphery of the membrane. As the blood passes through the gap plasma is filtered out into the interior of the spinner and packed blood cells which remain after plasma is removed are discharged from an outlet at the bottom or top of the housing. The plasma in the interior of the spinner passes through a bore in the lower pivot pin and is discharged from a central outlet port.

The spinner is rotatably supported by upper and lower pivot pin bearings and pivot pins which are conventionally made of stainless steel. An O-ring seal is loosely positioned between the spinner and the lower pivot pin bearing. In the conventionally employed stainless steel pin there are three important steps that must be performed carefully to insure the life of the seal. The first step involves machining a taper on the outside radius of the pin. This taper is required to prevent a steel edge from contacting and gouging an adjacent plastic wall when the pin rotates. The second involves the polishing of the end of the pin. This is accomplished by spinning the pin at a high rate of speed and applying a rubber abrasive for a certain length of time. Then the pin surface is brought to a mirror finish with a rouge polishing compound. The final part of this second step involves extensive cleaning of the pin to remove all polishing media and debris. The third step is the lubrication process. Both the pin and the O-ring are immersed in a diluted silicone oil solution. This silicone oil solution is specially tailored in both dilution and viscosity to provide sufficient lubrication without migrating to other undesirable areas of the blood separation filter. After all of the particulate matter has been cleaned from the pins, so that they are perfectly clean, the pins must be installed in devices and then sterilized by exposure to gamma radiation.

In order to avoid communication of disease the separation device is used only once and then discarded. Since the separation device is disposable it is desirable that it be manufactured as inexpensively as possible. However, since the upper and lower pivot pins for the rotor or spinner of these devices are fabricted from stainless steel, their initial raw material costs are relatively high. Further, the procedures for polishing, lapping the seal surface to minimize wear, and the cleaning of the pins greatly increases the cost of these pins. Moreover, the rejection rate for the processed stainless steel pins is surprisingly high, mainly due to the close tolerances which must be kept on the pivot pins in order for them to function properly together with the necessary tolerances required in molded plastic rotors.

SUMMARY OF THE INVENTION

A low cost, disposable plasmapheresis unit in accordance with the invention includes an outer shell or housing and a rotor including a rotating membrane supported within the sheel by a hard plastic injection molded pivot pin. The molded plastic material of the pivot pin has qualities of lubriciousness and hardness which enable the pin to withstand the stresses of supporting the rotor in high speed operation. The pivot pin is preferably constructed of a particular plastic material pointed out in detail hereinafter, which is capable of being injection molded. Such molding of the pivot pin from a suitable plastic is highly desirable since it avoids the many labor intensive preparation procedures noted above for stainless steel pivot pins. The inexpensive injection molding operation produces pins with sufficient smoothness and hardness on bearing surfaces while maintaining tight tolerances on critical dimensions.

In addition, molded plastic pivot pins produced according to the invention can be gamma irradiated not only for sterilization, but for modifying the polymer of the pivot pin to provide a surface having a low coefficient of friction so as to permit rotating of the spinning filter unit on the pivot pin for a length of time sufficient to provide required liquid separations.

The molded pivot pin, according to the invention is formed from a hard plastic having a low coefficient of friction. The pin has a lubricious wear resistant nature and will not create hot spots and will not shed debris. Such molded pivot pin is particularly useful in conjunction with a certain type of O-ring seal under the conditions of force which are required to be exerted to effect adequate sealing, and which will permit the device to operate for a sufficient length of time to permit the collection of the required amount of separated material, e.g. a typical volume of donated plasma, before discarding the unit.

BRIEF DESCRIPTION OF THE DRAWINGS

A better understanding of the invention may be had by reference to the following detailed description, taken in conjunction with the accompanying drawings, in which.

DETAILED DESCRIPTION OF THE INVENTION

Figure 1:
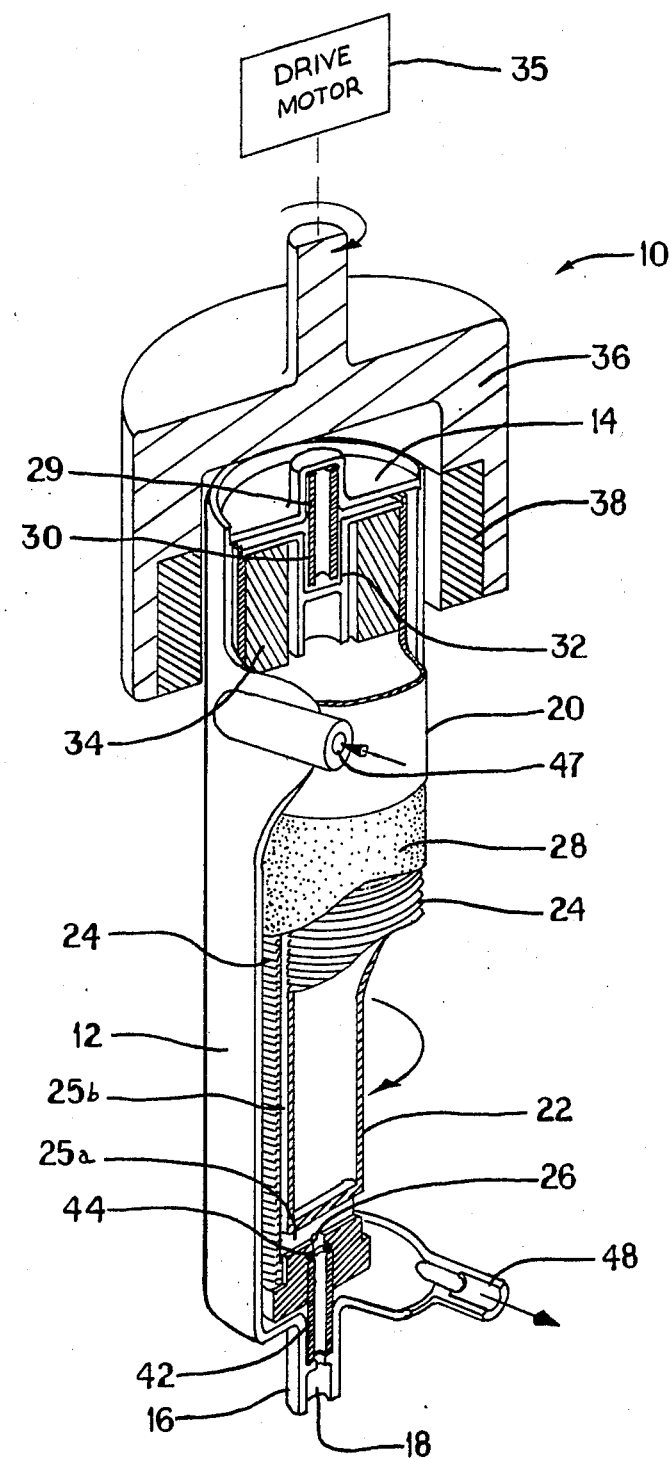
FIG. 1 is a perspective view, partly broken away, of a closed plasmapheresis disposable unit embodying the improved molded plastic pivot pin according to the invention.

Referring to FIG. 1 of the drawings, numeral 10 illustrates a disposable plasmapheresis device with which the pivot pin design of the invention can be employed. The device comprises a cylindrical housing 12 completed by an upper end cap 14, the walls of which are non-magnetic, and a bottom end housing 16 terminating in a plasma outlet port 18 concentric with a central axis of the device 10.

A generally cylindrical spinner or rotor 20 is mounted in a vertical position between the upper end cap 14 and the bottom end housing 16 for rotation about a rotor central axis which coincides with the central axis of housing 12. The spinner 20 comprises a shaped central mandrel 22, preferably of a light weight, strong, impermeable synthetic resin material such as high density polypropylene, acrylic, or ABS (acrylonitrile-butadiene-styrene resin). To simplify molding the spinner may be made in two separate pieces (not shown) that are joined together. The outer surface of the central mandrel 22 is shaped to define a series of spaced apart circumferential grooves or plasma channels 24 in the outer periphery of the mandrel. At each end of the mandrel 22 radially extending channels 25a provide communication between the periphery of mandrel 22 and a central orifice or manifold 26 concentric with the central axis. Axially extending grooves 25b in the periphery of the mandrel 22 interconnect the circumferential grooves 24 with the radial channels 25a to complete a network of interconnected paths between grooves 24 and manifold 26.

The surface of the rotary spinner 20 is covered by a cylindrical membrane 29 such as a commercially available filtration membrane of the type sold under the designation polyvinylidene fluoride by Millipore.

At its upper end, the rotary spinner 20 is rotationally supported relative to the upper end cap 14 by a stationary upper pivot pin 29 which is press fitted at its upper end into the end cap 14. The lower end of the pin 29 is seated within a cylindrical bearing surface 30 in an end cylinder 32 attached to or forming an integral part of the rotary spinner 20. The lower end of the pin 29 protrudes into a small chamber adjacent the bearing surface 30 so that the pin does not bind in the end cylinder 32. The end cylinder 32 is partially encompassed by a ring 34 of magnetic material such as stainless steel, utilized in indirect driving of the spinner 20. For this purpose, a drive motor 35 exterior to the housing 12 is coupled to turn an annular magnetic drive member 36 which partially surrounds the non-magnetic end cap 14. The drive member 36 includes diametrically opposed internal permanent magnets 38 so that as the annular drive member 36 is rotated, magnet attraction between the ring 34 interior to the housing and the magnets 38 exterior to the housing locks the spinner 20 to the exterior drive, causing the spinner to rotate without slippage. A rotational speed of the order of about 3600 rpm is used in this example, although higher rotational rates can be used.

Figure 2:
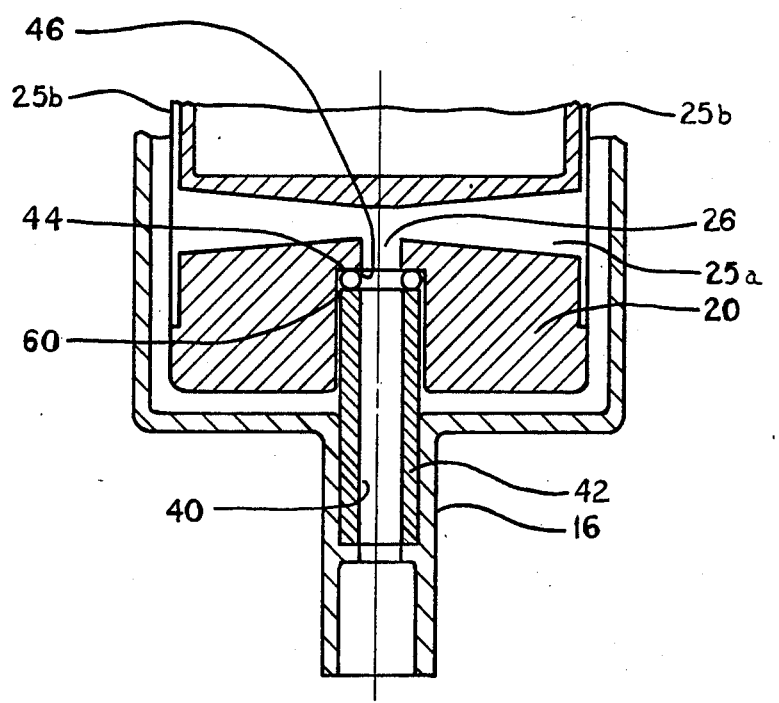
FIG. 2 is a sectional schematic detail of the lower portion of the rotor, the lower molded pivot pin of the invention and O-ring seal employed in the device of FIG. 1.

Referring particularly to FIG. 2, at the lower end of the rotary spinner 20, the central outlet orifice 26 communicates with a central bore 40 in a cylindrical lower end pivot pin 42 concentric with the central axis. The lower pivot pin 42 is seated in the bottom end housing 16. An O-ring seal 44 is mounted on an upper end surface of the pivot pin 42 and an internal shoulder 46 at the lower end of the rotor 20 rests on top of the O-ring seal 44. The O-ring seal is fabricated preferably of a Viton material, a series of fluoroelastomers based on the copolymer of vinylidene fluoride and hexafluoropropylene, marked by DuPont, and is specifically formulated for medical applications. The O-ring is covered with a silicone lubricant to provide sufficient lubrication. Thus, the rotor 20 and the O-ring 44 ride on top of the pivot pin 42, and the rotor is thus supported at its center of rotation by the upper and lower pins 29 and 42.

The pivot pin 42, according to the present invention, is in the form of a plastic pivot pin molded from suitable organic polymers which confer certain important characteristics on the pivot pin as described in greater detail hereinafter. The upper pivot pin 29 is preferably of the same configuration and molded of the same polymers as the lower pivot pin 42. Although it is not essential that the upper pin be hollow use of the same part at both ends reduces cost of the disposable.

Referring again to FIG. 1, in operation, with the rotary spinner 20 rotating, for example at 3600 rpm, whole blood is fed through the input port 47 which directs the blood into a region or space between the spinner 20 and the outer wall of the housing 12. The plasma is filtered through the cylindrical membrane 28 into the interior of the spinner and passes downwardly through the central orifice or manifold 26 and is discharged through the outlet port 18. Packed blood cells with the plasma removed is discharged via the outlet port 48 at the bottom of the device. A plasmapheresis device of the type described above is described and claimed in detail in the above-identified copending Fischel application.

It will be noted, referring to FIG. 2, that the weight of the rotor 20 is supported on the O-ring seal 44 which rides on an upper end of the lower pivot pin 42. In operation of the plasmapheresis device, there are two components of downward force on the rotor against the O-ring required in order to provide effective sealing without leakage. The first is the weight of the rotor and the second is a downward force generated by the interaction of the magnetic coupling device 34 in the rotor with the magnetic drive 38. It has been found in the specific plasmapheresis device of the present invention that these two forces should add up to a force in the range of 1000-1800 grams per square cm of seal contact area. In the present example this corresponds to between 370 and 450 grams of total force. It has been found empirically that this seal force is necessary to prevent leakage of red cells exterior of the filter membrane 28 into the separated plasma in the central plasma channel 26 of the hollow rotor 20 and to prevent leakage of the plasma through the seal and back into the red cell rich blood. However, too much seal force causes premature wear-out of the O-ring seal.

Figure 3:
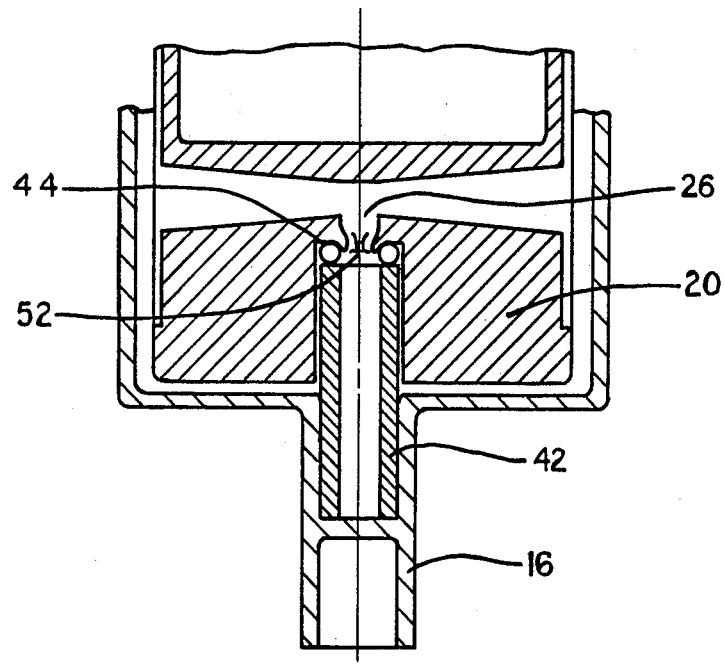
FIG. 3 is a sectional detail view similar to FIG. 2, showing a typical wear pattern of the plastic rotor employing the pivot pin having the design shown in FIG. 2.

Tests have shown that when the lower pivot pin 42 is in the form of a cylinder as shown in FIG. 2, although in most cases it operates satisfactorily, significant wear of the plastic rotor on the seal ring occurs in some few instances. Thus, referring to FIG. 3, in a small percentage of cases, friction between the pivot pin 42 and the O-ring 44 and between the pivot pin 42 and the rotor 20 generates sufficient heat to deform the plastic of the rotor, as indicated by deformation 52. One result of such deformation is that the plastic outlet port at 18 can partially occlude itself. Experiments have shown that there is no adverse effect on the blood as this happens since only plasma flux will be restricted and the instrument controllers automatically adjust for this. However, the procedure must be terminated when flow becomes too badly restricted.

Figure 4:
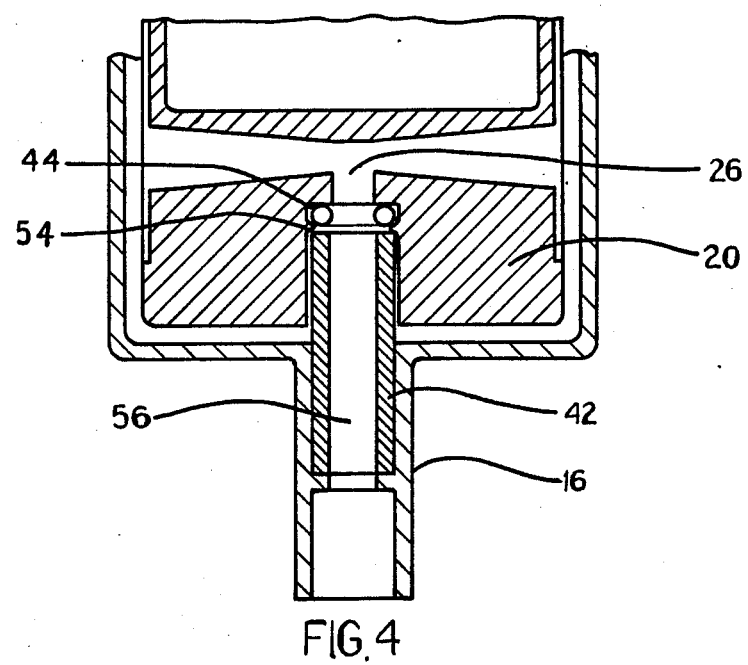
FIG. 4 is a view similar to FIG. 2, showing the phenomenon termed "ridge wear," which occurs on the plastic rotor when employing the pivot pin having the configuration shown in FIG. 2.

Another phenomenon which occurs in some instances when employing the combination of plastic rotor, Viton O-ring and non-tapered stainless steel pivot pin of FIG. 2 is the phenomenon termed herein "ridge wear" illustrated in FIG. 4. In this respect, a ridge of plastic, indicated at 54, forms the action of the rotor 20 spinning around the pivot pin 42. The pin 42 is not always installed perfectly perpendicular to the axis of rotation and this misalignment of the pin 42 causes the rotor plastic to "see" an up-down motion at the edge of the pin 42. That is, the circumferential edge of the upper end of pin 42 has an apparent oscillating axial motion relative to a point on the rotor 20 as rotor 20 rotates about pin 42. This apparent motion presents a problem because as the ridge 54 increases in size it forms a ring of plastic between the pivot pin 42 and the O-ring 44, thus losing the integrity of the seal, and allowing red cells to pass into the central plasma channel 56 of the pivot pin. If this should happen in usage a microprocessor controlling system operation in response to an optical plasma detector will sense either red cells or hemoglobin (broken cells) and alert the operator to discontinue the procedure without risk to the donor. It is important to note that the "ridge wear" is isolated to the area of the rotor around the pivot pin and no wear material enters the blood or plasma.

Figure 5:
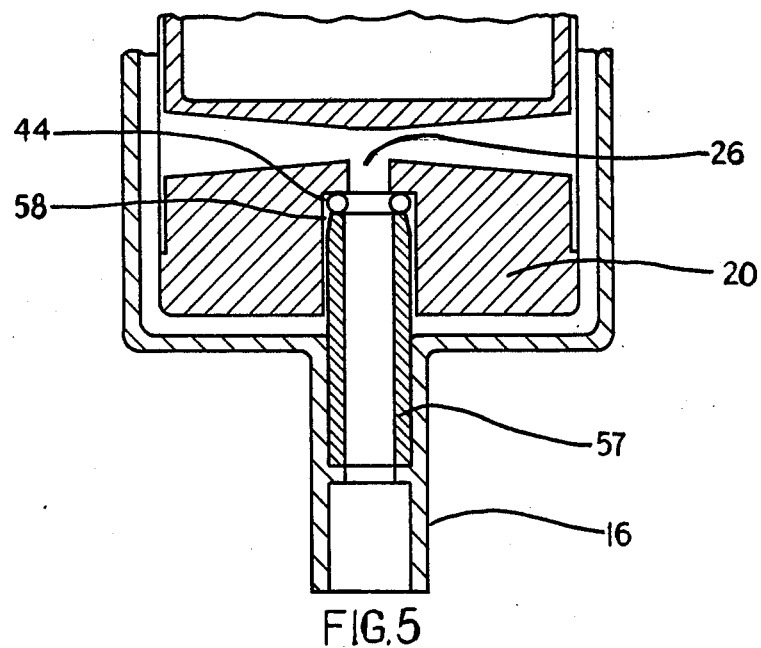
FIG. 5 is a view similar to FIG. 2, illustrating the preferred configuration of the tapered molded plastic pivot pin employed in the invention device.

Referring now to FIG. 5 it has been found that providing a slight upper taper or cone shape at 58 at the top of the molded plastic pivot pin 42 of FIG. 2 removes the sharp contact edge noted at 60 in FIG. 2, from the plastic pivot pin bearing 42 of the invention, thus permitting the pin to be slightly off the vertical axis of the rotor, and yet not cause the ridge wear phenomenon noted in FIG. 4. Accordingly, the improved design of the plastic molded hollow pivot pin indicated at 57 in FIG. 5 is the preferred embodiment.

The plastic pivot pin indicated at 42 in FIG. 2 and at 57 in FIG. 5, according to the invention, is a molded pivot pin of a hard plastic material having a low coefficient of friction and having lubriciousness and wear resistance, so that the rotor spinning against the plastic pin does not create hot spots on the pin or shed debris.

Another important consideration is that the entire fluid separation device is irradiated by gamma radiation, as by a cobalt 60 source, not only for sterilization purposes, but for additional polymer modification of the plastic pivot pin, without degradation or loss of the lubricious properties of the pivot pin.

In this respect it has been found that few plastics retain the same properties after a normal dosage of gamma radiation used in sterilization. Most plastics become very brittle, lose their lubricious properties, and some turn to dust. On the molecular level, the two most prevalent things which occur are chain scission or crosslinking. The scission is usually exhibited by the polymer losing impact and tensile strength. The crosslinking of a polymer chain shows an increased brittleness, or sometimes increased strength. Thus, for example, it was found that certain materials such as polyimide (Torlon) are virtually unchanged by gamma radiation at the levels used for biological sterilization. However, such material can only be extruded and machined. Since such processing retains much of the same cost intensiveness as the prior art stainless steel pins, polyimide was found unsatisfactory.

Another criterion is that it is necessary to conform to the F.D.A. toxicity requirements for blood compatibility and donor safety. There has been significant work accomplished in the field of polymer science in development of inherently lubricated polymers for wear applications, including the use of base polymers with various additives, including, for example, polytetrafluoroethylene, silicone, glass fiber and carbon fiber.

Development work was undertaken employing existing plastics developed for lubrication characteristics and pivot pins were machined from these materials. In addition to machined pivot pins formed from polyimide (Torlon and Envex) noted above, plastics such as Delrin (acetal resins), PVC (polyvinyl chloride), and polycarbonate were tried. While certain of these materials such as Torlon performed very well, others such as PVC and polycarbonate did not wear well against the O-ring seal. In addition, certain materials such as Envex possessed problems in that they could not be molded economically and therefore manufacture of inexpensive parts from such materials was rendered difficult.

After trying a number of machined plastic pivot pins, it was found that plastic pivot pins having the above noted required properties for use in biomedical applications could be economically produced by injection molding of suitable polymer materials. In addition, certain plastics, for example the modified plastics marketed by LNP Corporation, of Malvern, Pa., such as RL 4730, also possess certain desirable characteristics when molded, as opposed to being machined. Properties such as the "skinning effect" to the outside of the injection molded plastic material make it a very low friction surface.

A number of tests were carried out using unradiated injection molded pivot pins and injection molded pivot pins which were gamma irradiated with 2.5 Megagrads of radiation, employing various polymers. The results of these tests are shown in the Table below.

TABLE

| Chemical Composition | Marketed As | Results |
|---|---|---|
| MOLDED PINS UNRADIATED | | |
| Polycarbonate with PTFE | DL 4040 | Molding problem O-ring wears ripples into end of pin. |
| Polyester | Valox 312 | Wear on the end of the pin excessive debris generated. |
| Polyamide carbon fiber with PTFE | RCL 4536 | Pin wears well but wears out ABS rotor. Fibers in the pin material abrade the plastic of the rotor and the O-ring. |
| Polyester with PTFE | WL 4040 | Pin sheds debris and wears excessively. Pin spin welds to inside of rotor. |
| | WL 4410 | Pin and rotor bearing wear |
| | WL 4510 | Unacceptable pin wear |
| | WL 4620 | Unacceptable pin wear |
| Nylon 6/12 | IL 4510 | Pin debris |
| Polyamide | RL 4730 | Intermittent failures and successes |
| MOLDED PINS GAMMA IRRADIATED | | |
| | WL 4620 | Unacceptable wear |
| Polyester | WL 4410 | Unacceptable wear |
| | IL 4510 | Mixed results - good and bad runs |
| | WL 4510 | Pin and rotor bearing failure |
| Nylon 6/6 | RL 4730 | Excellent runs with occasional but acceptable wear |

From the Table above, in the tests with the molded pins which were unradiated, the results showed unacceptable pin and rotor wear in a number of cases and excessive debris generation in many others. It thus appeared that no pivot pins formed of unradiated polymers provided a performance which would be adequate for use in the plasmapheresis device of the invention.

In the tests with the molded pins which were gamma irradiated, in most cases the pivot pins thus created and tested in the plasmapheresis device resulted in unacceptable wear and pin and rotor bearing failure. However, one of the molded polymers of this latter group of polymers which were tried, namely Nylon 6/6 and RL 4730, a polyamide based polymer modified with PTFE and Silicon gave excellent runs and was found least susceptible to wear when employed in the plasmapheresis device described above.

Other polymers capable of being injection molded, and after irradiation in the manner described above also provided suitable results. These polymers include ULTEM EL 4040.

It is not understood as to why only certain polymers, particularly those which are capable of being injection molded, and having the desired characteristics noted above, including the ability to be gamma irradiated, without adverse effects, are suitable for the purpose of the invention.

From the foregoing, it is seen that the invention provides a novel combination of plastic spinner and molded plastic pivot pin bearing, in conjunction with an O-ring seal, which is highly advantageous and applicable particularly for use in biomedical applications where it is necessary to separate fluids, as by filtration, e.g. in hemapheresis, in a closed environment employing a seal, and where the device is disposable. The invention resides particularly in the provision of an economical plastic molded pivot pin which is sufficiently hard and lubricious, in conjunction with an O-ring seal, preferably covered with a silicone lubricant, such as to permit operation of the separation unit for a sufficient period under the conditions of force which has to be exerted, to collect the required amount of product, e.g. units of plasma, after which the device is discarded.

Since various changes and modifications of the invention will occur to and can be made readily by those skilled in the art without departing from the invention concept, the invention is not to be taken as limited except by the scope of the appended claims.

What is claimed is:

1. In a disposable biomedical system for processing fluids in a closed environment including a plastic rotor mounted for rotation on a pivot pin and a seal between the rotor and pivot pin, an improvement comprising: said pivot pin being molded of a hard plastic material having a low coefficient of friction and lubriciousness, and which has been irradiated by gamma radiation for sterilization and ploymer modification of the plastic material to increase lubriciousness sufficient for operating in a disposable biomedical fluid separation system.

2. The system of claim 1, said seal being a silicone lubricated O-ring and the pivot pin being substantially cylindrical and hollow to permit passage of liquid.

3. The system of claim 2, in the form of a hemapheresis system for the filtration of plasma from whole blood, wherein the rotor comprises a spinner covered with a filter membrane and wherein plasma from whole blood is filtered through the membrane into the center of the spinner and passes downwardly through the hollow pivot pin.

4. The system of claim 2, the pivot pin being tapered adjacent to the seal.

5. The system of claim 1, wherein said pivot pin is formed of an injection molded polyamide based resin.

6. The system of claim 1, said rotor, seal and pivot pin mounted within a housing and including magnetic means coupled to the rotor within the housing, and external drive means magnetically coupled to the magnetic means for rotating the rotor within the housing, the weight of the rotor supported on the seal and an additional downward force on the rotor against the seal being generated by the interaction of the magnetic means in the rotor with the external drive means, providing sufficient sealing force to compress the seal and provide protection against leakage.

7. The system of claim 6, the total sealing force being between 1000 and 1800 grams per sq. cm of seal contact area.

8. A system comprising:
 means providing a disposable membrane filtration system for the separation of plasma from whole blood in a closed housing, including:
 a spinner covered with a filter membrane, and wherein plasma from whole blood is filtered through the membrane into the center of the spinner and passes downwardly through the spinner;

a lower substantially cylindrical pivot pin supporting the spinner for rotation thereon, said pivot pin having a central bore for passage of the plasma from the center of the spinner, said pivot pin being injection molded of a hard plastic material having a low coefficient of friction and lubriciousness, and which has been irradiated by gamma radiation for sterilization and modification of the plastic material to improve lubriciousness sufficient for operating in a disposable biomedical fluid separation system;

a silicone lubricated O-ring seal disposed between the spinner and an end surface of the pivot pin;

said spinner, seal and pivot pin being mounted within a housing including magnetic means coupled to the rotor within the housing and external drive means magnetically coupled to the magnetic means for rotating the spinner within the housing; and the weight of the rotor supported on the seal and an additional downward force on the rotor against the seal being generated by the interaction of the magnetic means in the rotor with the external drive means providing sufficient sealing force to compress the seal and provide protection against leakage.

9. The system of claim 8, the total sealing force being between 370 and 450 grams.

10. The system of claim 8, the pivot pin being tapered at the top adjacent to the seal.

11. The system of claim 8, wherein said pivot pin is formed of an injection molded polyamide based resin.

12. The system of claim 8, the pivot pin being tapered at the top adjacent to the seal, and wherein said pivot pin is formed of an injection molded polyamide, the total sealing force being between 370 and 450 grams.

13. The system of claim 8, including an upper end cap mounted in said housing and an upper pivot pin press fitted into said cap, said upper pivot pin being injection molded of a hard plastic material of the same composition as said lower pivot pin, an end cylinder on the upper end of said spinner, said upper pivot pin seated in a bearing surface of said end cylinder, said lower pivot pin being fixedly seated in the base of said housing, the spinner being supported at its center of rotation by the upper and lower pivot pins.

14. The system of claim 13, wherein said upper and lower pivot pins are each formed of an injection molded polyamide based resin.

15. The system of claim 14, wherein the lower pivot pin is tapered at the top adjacent to the seal, the total sealing force being between 370 and 450 grams.

16. A disposable biomedical fluid filtering device comprising:
   a housing having a fluid inlet and two fluid outlets;
   a filtering rotor rotationally disposed within said housing for filtering a filtrate from a biomedical fluid fed into said inlet and for providing said filtrate at a predetermined one of said flid outlets;
   means designed for reducing the cost of the manufacturing steps of said disposable biomedical fluid filtering device including at least one injection molded hollow pivot pin formed of a polyamide-based resin and irradiated for sterilization and for increased lubriciousness sufficient for operating in a disposable biomedical fluid separation system,
   said rotor being rotationally mounted onto said pivot pin with an O-ring seal located between the rotor and an end of the pivot pin for permitting rotation of the rotor within said housing and for passing said filtrate through said hollow pivot pin to said predetermined one of said fluid outlets.

17. A disposable biomedical fluid filtering device as in claim 16 wherein said pivot pin is formed as a hollow cylindrical structure having a frusto-conically shaped outer end surface.

18. A disposable biomedical fluid filtering device as in claim 17 wherein said polyamide-based resin is one of the group comprising Nylon 6/6 (RL 4730) and ULTEM (EL 4040).

19. An improved plastic pivot pin of reduced cost but high reliability and economical manufacture for use in a disposable biomedical system for processing fluids in a closed environment having a plastic rotor mounted on said pin for rotation with respect to a housing enclosure, said pin comprising: an injection molded hollow cylindrical structure having a frusto-conical outer end, being molded of a polyamide-based resin and also having been irradiated for sterilization and increased lubriciousness sufficient for operating in a disposable biomedical fluid separation system, and means for enabling said pin to operate in said system.

20. A disposable plasmapheresis device comprising:
   a housing having a fluid inlet and two fluid outlets;
   a filtering rotor rotationally disposed within said housing for filtering plasma from blood fed into said inlet and for providing said plasma at a predetermined one of said fluid outlets;
   means designed for reducing the cost of the manufacturing steps of said disposable plasmapheresis device including at least one injection molded hollow pivot pin formed of a polyamide-based resin and irradiated for sterilization and for increased lubriciousness sufficient for operating in a disposable biomedical fluid separation system,
   said rotor being rotationally mounted onto said pivot pin with an O-ring seal located between the rotor and an end of the pivot pin for permitting rotation of the rotor within said housing and for passing filtered plasma through said hollow pivot pin to said predetermined one of said fluid outlets.

21. A disposable plasmapheresis device as in claim 16 wherein said pivot pin is formed as a hollow cylindrical structure having a frusto-conically shaped outer end surface.

22. A disposable plasmapheresis device as in claim 17 wherein said polyamide-based resin is one of the group comprising Nylon 6/6 (RL 4730) and ULTEM (EL 4040).

* * * * *